(12) United States Patent
Matsubara et al.

(10) Patent No.: US 9,302,119 B2
(45) Date of Patent: Apr. 5, 2016

(54) LIGHT-BEAM THERAPEUTIC APPARATUS

(71) Applicant: ATOM MEDICAL CORPORATION, Tokyo (JP)

(72) Inventors: Kazuo Matsubara, Tokyo (JP); Terumi Matsubara, Saitama (JP); Naoki Honma, Saitama (JP); Hiroki Suma, Saitama (JP); Yoshiyuki Tashiro, Saitama (JP)

(73) Assignee: ATOM MEDICAL CORPORATION, Tokyo (JP)

( * ) Notice: Subject to any disclaimer, the term of this patent is extended or adjusted under 35 U.S.C. 154(b) by 290 days.

(21) Appl. No.: 13/799,149

(22) Filed: Mar. 13, 2013

(65) Prior Publication Data
US 2013/0325087 A1 Dec. 5, 2013

(30) Foreign Application Priority Data
Jun. 1, 2012 (JP) ................................. 2012-125944

(51) Int. Cl.
*A61N 5/06* (2006.01)
(52) U.S. Cl.
CPC ......... *A61N 5/0621* (2013.01); *A61N 2005/063* (2013.01); *A61N 2005/0626* (2013.01); *A61N 2005/0652* (2013.01)
(58) Field of Classification Search
CPC .................... A61N 2005/0645; A61N 5/0616; A61N 2005/063

USPC ........................................................ 607/88, 89
See application file for complete search history.

(56) References Cited

U.S. PATENT DOCUMENTS

2007/0239232 A1\* 10/2007 Kurtz et al. ..................... 607/87

FOREIGN PATENT DOCUMENTS

| JP | 2005-056608 | 3/2005 |
| JP | 2006-217990 | 8/2006 |
| JP | 2006-223665 | 8/2006 |

\* cited by examiner

*Primary Examiner* — Aaron Roane
(74) *Attorney, Agent, or Firm* — Wenderoth, Lind & Ponack, LLP.

(57) ABSTRACT

A light-beam therapeutic apparatus used for a therapy for neonatal hyperbilirubinemia is disclosed, which includes an apparatus body portion having a light source; a light guide rod that guides light from the light source, a connecting socket, a cooling fan, an electronic component that performs control required for a therapy, and a control display panel that displays the contents of therapy; a therapeutic portion including a light guide portion including a plurality of bundled optical fibers, and a pad portion formed of the optical fibers spread out adjacently to one another into a flat-panel shape, and the therapeutic portion is formed into a light-receiving plug insertable into a connecting socket of the apparatus body portion, and the optical fibers positioned on the pad portion are subjected to exposing processing and have a protecting surface layer portion formed of a bag member filled with transparent and highly flexible high-molecular gel.

6 Claims, 7 Drawing Sheets

LIGHT-BEAM THERAPEUTIC APPARATUS

BACKGROUND OF THE INVENTION

1. Field of the Invention

The present invention relates to a therapeutic apparatus used mainly for a therapy for neonatal hyperbilirubinemia and, for example, to a light-beam therapeutic apparatus configured to perform a therapy by introducing a therapeutic light beam from a light source to a pad portion for placing a neonatal infant via an optical fiber, and dispersedly radiating the therapeutic light beam from the pad portion.

2. Prior Art

A plurality of medical light-beam therapeutic apparatuses of this type configured to perform a therapy by guiding a light beam from a light source to a therapeutic portion via an optical fiber as described below, although not a pad-type, are known.

As a first known technology, there is proposed a light irradiating apparatus or a light-beam therapeutic apparatus including an apparatus body portion having a light source, a light guide portion extending from the apparatus body portion, and a hand piece coupled to the light guide portion on the side opposite from the apparatus body portion, and configured to irradiate an object to be irradiated with light from the hand piece, characterized in that the light guide portion is composed of an optical fiber bundle having bundled optical fibers, and a light-homogenizing member configured to substantially homogenize an output distribution of irradiation light from the optical fiber bundles is disposed in the interior of the hand piece portion (see JP-A-2005-56608).

In the light-beam therapeutic apparatus of the first known technology, since the therapy is achieved by irradiating affected areas of human bodies or animals with a substantially homogenized output light, therapeutic effects desirable for a medical application which requires a homogenous output light distribution such as a thermal therapy for joint pain or bedsore by means of infrared ray, treatment of macula by means of laser beams may be expected. In particular, this apparatus is effective when treating tissues of cancer or the like by a photo dynamic therapy (PDT) because light irradiation with high homogeneity is possible. In addition, since the irradiation is achieved from many angles freely by the optical fiber bundle, the operability is superior.

A second known technology is a light-beam therapeutic apparatus including a light source, a plurality of first optical fibers optically connectable with the light source, a plurality of probes optically connected to the plurality of first optical fibers respectively, and a light guide controller configured to switch the first optical fiber to be optically connected to the light source from among the plurality of first optical fibers (see JP-A-2006-223665).

In the light-beam therapeutic apparatus of the second known technology, an affected area may be irradiated with a light-beam output from the light source from each of the plurality of probes without attenuating the output. Therefore, a therapy for a deep portion of a body is facilitated and reduction of therapeutic time is achieved. In addition, since irradiation from the plurality of probes is achieved using a single light source, relatively low production costs are achieved in comparison with the light-beam therapeutic apparatus of the prior art that requires the same number of light sources (for example, laser elements) as the probes.

A third known technology is a light-beam therapeutic apparatus including an optical system configured to converge and guide light from a plurality of different light sources, an optical fiber cable configured to multiply carry the converged and guided light, and a hand piece including at least one projector lens configured to project output light from a distal end of the optical fiber cable disposed therein (see JP-A-2006-217990).

In the light-beam therapeutic apparatus of the third known technology, the plurality of light sources are provided intensively into one machine and hence space saving is achieved. Light in a plurality of different wavelength regions may be combined as needed.

In the light-beam therapeutic apparatus of the first known technology, the light guide portion is composed of the optical fiber bundle including bundled optical fibers, a light-homogenizing member configured to substantially homogenize the output distribution of the irradiation light from the optical fiber bundle is installed in the interior of the hand piece portion, so as to perform a therapy by irradiating the visible affected area with homogenous and spot-like output light, and is not an apparatus which performs a therapy over an invisible wide range, specifically, even for a portion of a neonatal infant in a state of being laid down coming into abutment with a mat or the like with dispersed light.

The light-beam therapeutic apparatus of the second known technology is configured to be capable of irradiating the affected area in the body with the light-beam output from the single light source through each of the plurality of probes without attenuating the output on the basis of time division and, specifically, the laser beams are converged so as to reach the deep portion of the body. Therefore, this apparatus is not intended to perform a therapy for a wide range with a dispersed light.

In order to achieve the space saving, the light irradiating apparatus of the third known technology is configured to include the plurality of different light sources provided intensively into a single machine, a single multiple-carrying optical fiber cable configured to optically converge and guide light from these light sources, and a lens configured to project the combined light in the plurality of different wavelength regions from the distal end of the optical fiber cable and irradiate the affected area with the combined light, and is not an apparatus which performs a therapy with diffused light over an invisible wide range, specifically, even for a portion of a neonatal infant in a state of being laid down coming into abutment with a mat or the like.

SUMMARY OF THE INVENTION

Accordingly, it is an object of the invention to provide a light-beam therapeutic apparatus configured to be capable of performing a therapy for a hidden invisible portion of the body so as to be applicable to the therapy for neonatal hyperbilirubinemia.

In order to solve the above-described problem, there is provided a light-beam therapeutic apparatus of the invention including: an apparatus body portion having at least a light source, a light guide rod configured to guide light from the light source, a connecting socket to which an end portion of the light guide rod faces, a cooling fan configured to cool the light source, an electronic component configured to perform control required for a therapy, and a control display panel configured to display the contents of therapy being set by operating the electronic component, and a therapeutic portion including a light guide portion having a plurality of bundled optical fibers, and a pad portion formed of the optical fibers adjacently to each other and spread out into a flat-panel shape, wherein an end portion of the light guide portion of the therapeutic portion is formed into a light-receiving plug insertable into the connecting socket of the apparatus body portion, and the optical fibers positioned on the pad portion are subject to exposing processing and are provided with a protecting surface layer portion formed of a bag member filled with transparent and highly flexible high-molecular gel.

Preferably, the optical fiber has a two-layer structure including a core layer on an inner side thereof and a clad layer on an outer periphery thereof, and the exposing processing breaks parts of the clad layer.

Further preferably, the light-receiving plug of the light guide portion is provided with a translucent thermal insulation member at an end portion thereof, and the pad portion is covered with a pad cover when in use.

Since the light-beam therapeutic apparatus of the invention is configured to be capable of irradiating light homogeneously and efficiently by performing the exposing processing on the optical fibers of the pad portion spread into the flat panel shape, a superior effect that a neonatal infant having hyperbilirubinemia laid on the pad portion on his or her back, for which the therapy cannot be performed usually because it is hidden, may be irradiated with homogeneous light beams entirely, and hence an efficient and adequate therapy is performed, is exhibited.

Since the light-beam therapeutic apparatus of the invention is provided with the protecting surface layer portion formed of the bag member filled with transparent and high-flexible high-molecule gel on an upper surface of the pad portion, even when the neonatal infant laid thereon moves, the neonatal infant is gently held by the protecting surface layer portion, and hence the therapy may be performed without causing damage or bedsore on the skin of the neonatal infant.

DETAILED DESCRIPTION OF THE INVENTION

Figure 1:
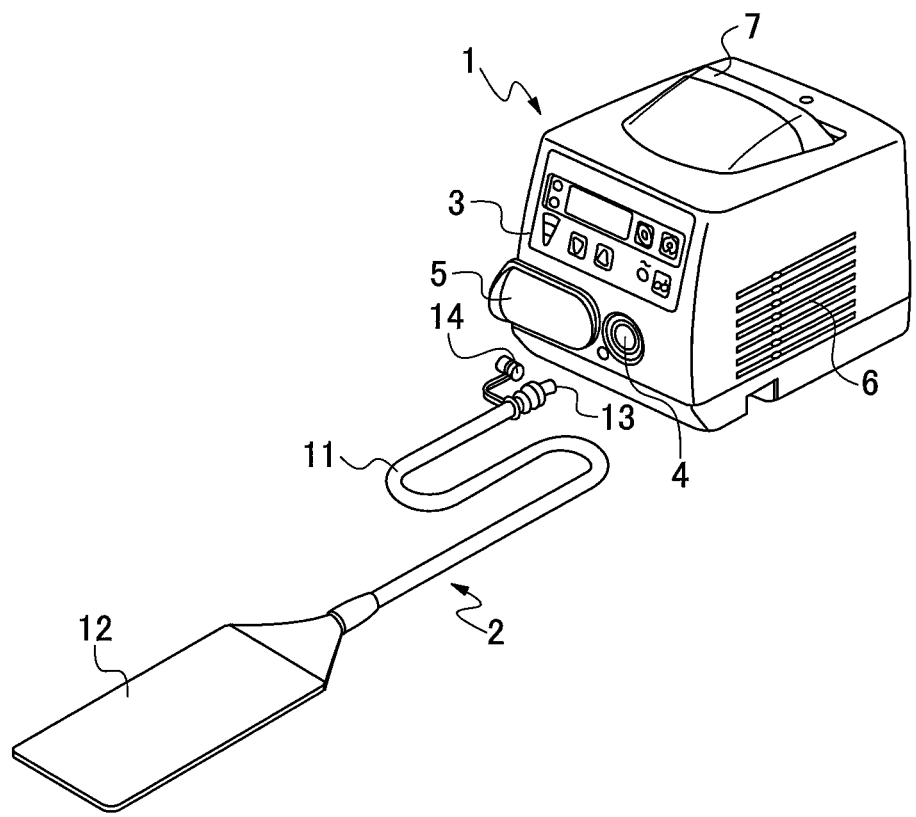
FIG. 1 is a perspective front view of a light-beam therapeutic apparatus according to an embodiment of the invention illustrating a state in which an apparatus body portion and a therapeutic portion are separated.
Figure 2:
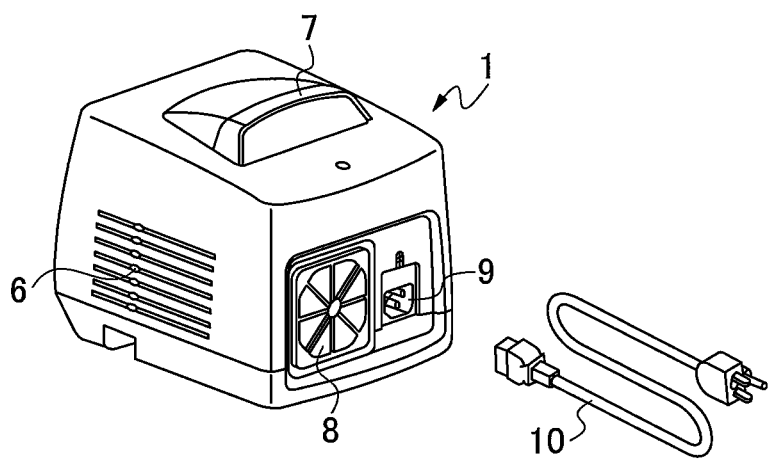
FIG. 2 is a perspective back view of the same light-beam therapeutic apparatus illustrating a state in which the apparatus body portion and a power source cord are separated.

Referring now to an embodiment illustrated in the drawings, the invention will be described. In FIGS. 1 and 2, a light-beam therapeutic apparatus according to the invention includes an apparatus body portion 1 and a therapeutic portion 2 configured to be connectable and disconnectable with respect to the apparatus body portion 1.

The apparatus body portion 1 includes a control display panel 3 as an operating section provided on the front side, a connecting socket 4 of the therapeutic portion 2, and a slide-type shutter 5 configured to open and close the connecting socket 4, a ventilating opening 6 provided on both side surfaces and a bottom portion thereof, and a grip portion 7 provided on an upper surface thereof. In addition, on the back side, a filter 8 for air supplied by a cooling fan and a power source socket 9 is provided, and a suitable power source cord 10 is connected to the power source socket 9.

The therapeutic portion 2 includes a light guide portion 11 including a plurality of flexile optical fibers bundled into a rod shape, and a pad portion 12 formed into a flat shape by placing the optical fibers from the light guide portion 11 in alignment in a spread manner to allow a neonatal infant to be placed thereon and configured to emit light substantially homogenously as a whole. A free end side of the light guide portion 11 is formed into a shape of a light-receiving plug 13, and in the vicinity of the light-receiving plug 13, a suitable cap 14 is provided so as to cover the light-receiving plug 13 for protecting the optical fibers.

Figure 3:
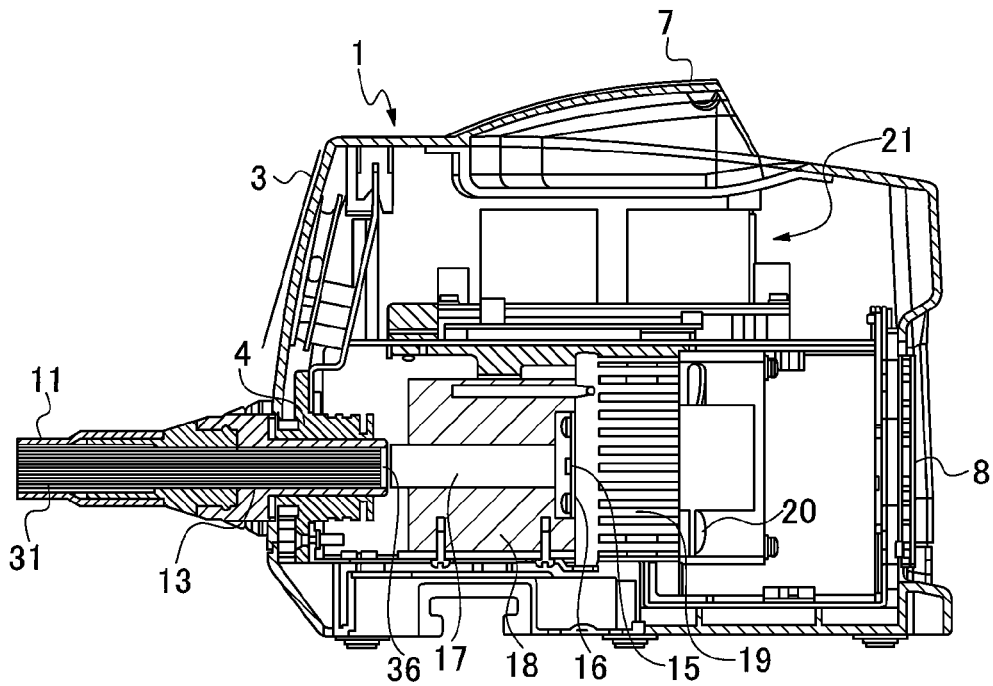
FIG. 3 is a partly omitted vertical cross-sectional view of the same light-beam therapeutic apparatus illustrating a state in which the apparatus body portion and the therapeutic portion are connected.

The apparatus body portion 1 includes, as illustrated in FIG. 3, a substrate 16 on which a light source 15 composed of blue light-emitted LEDs, for example, is mounted in the interior thereof, and a light guide rod 17 of core clad specifications configured to guide light so as to prevent from being scattered is disposed on the light-emitting side of the light source 15, that is, on the front side via a mounting member 18, and a distal end portion of the light guide rod 17 opposes the connecting socket 4. The substrate 16 is mounted in tight contact with a heat radiating member 19 for radiating heat of the light source 15, a cooling fan 20 for supplying air for cooling and thermal radiation is disposed on the back side of the heat radiating member 19, and, in addition, a plurality of electronic components 21 required for controlling the function of the apparatus body portion 1 are mounted thereon.

Figure 4:
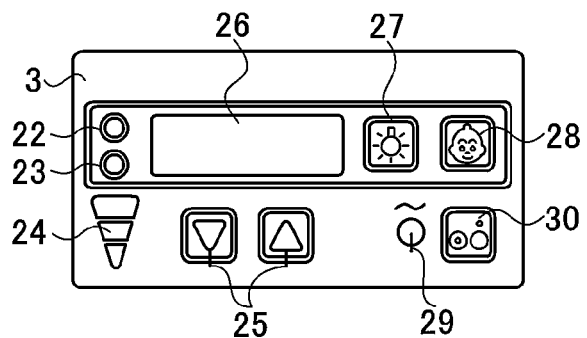
FIG. 4 is a front view of the same light-beam therapeutic apparatus illustrating a control display panel.

As illustrated in FIG. 4, the control display panel 3 includes a lamp (light source) time display lamp 22, a patient irradiation time display lamp 23, a light adjustment display portion 24 for displaying high, medium, and low, a light-adjustment button 25, a display unit 26 for displaying irradiation time or messages, a lamp button 27, a patient button 28, a pilot lamp 29, and a power source switch 30, and is configured to allow the operation of the function controlling electronic components 21 described above and setting the function of the apparatus body portion 1 to a therapeutic state suitable for the patient, and allow any medical staff to visually confirm the therapeutic state of the patient at any time from the control display panel 3.

Figure 5:
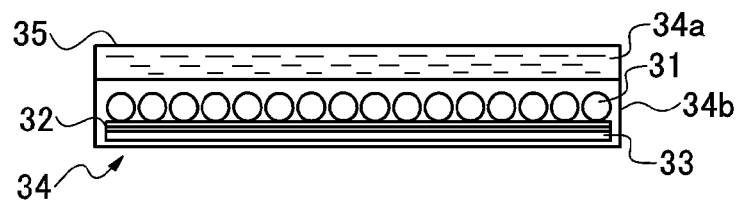
FIG. 5 is a vertical cross-sectional view illustrating a pad portion of the therapeutic portion of the same light-beam therapeutic apparatus.

As illustrated in FIG. 5, the pad portion 12 of the therapeutic portion 2 is formed by placing a plurality of optical fibers 31 (for example, PJR-FB500 manufactured by TORAY INDUSTRIES, INC.) connected from the light guide portion 11 in proper alignment flatly and adjacently to one another, adhering the optical fibers 31 placed in adjacent alignment to one another on a flexible sheet-shaped high-reflective member 33 (for example, RAY BRIGHT RB97UN-BM manufactured by ATT) using an adhesive device 32, for example, a double-faced adhesive tape (for example, a double-faced tape 1510 for skin manufactured by 3M), and fixedly securing the same in a stable state. Subsequently, the exposing processing is applied to the upper surfaces of the optical fibers 31 secured in the aligned manner and the entire part is covered with a bag-shaped cover member 34 formed of a translucent flexible sheet member. In this case, the pad portion 12 is formed by using the bag-shaped cover member 34 formed with two flat upper and lower layers of bag members 34a and 34b partitioned by a non-yellowing high-transparent and high flexible urethane sheet as the translucent flexible sheet member, filling the bag member 34a on the upper side with high-molecular gel such as non-yellowing transparent and flexible urethane gel or styrene gel to form a protecting surface layer portion 35, and inserting and storing the optical fibers 31 fixedly secured to the high-reflective member 33 and subjected to the exposing processing in the bag member 34b on the lower side.

Four types of processing are contemplated as the exposure processing with respect to the optical fibers 31.

Figure 6A:
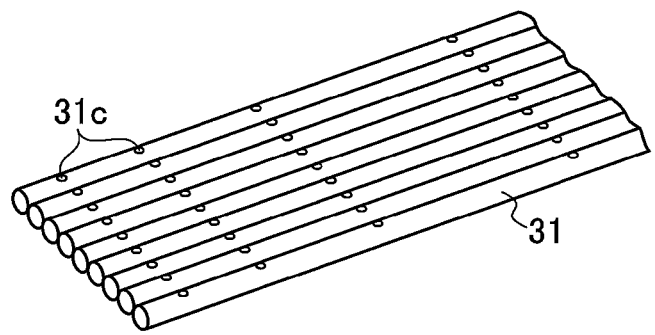
FIG. 6A is a perspective view illustrating a part of an example of a first exposed process of an optical fiber configuring the pad portion of the therapeutic portion of the same light-beam therapeutic apparatus.
Figure 6B:
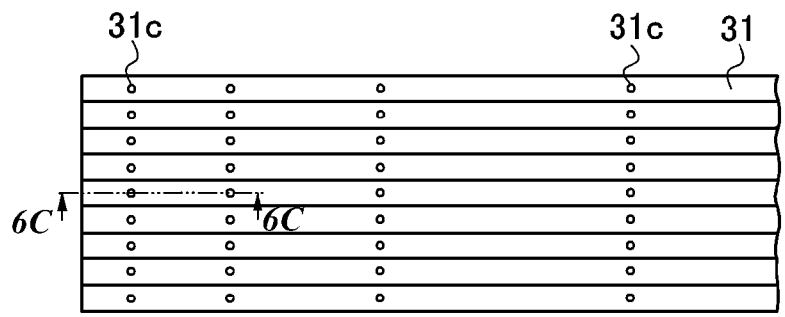
FIG. 6B is a plan view of the optical fiber illustrated in FIG. 6A.
Figure 6C:
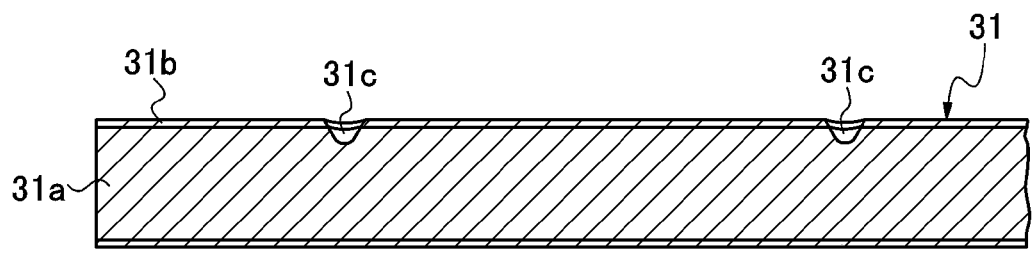
FIG. 6C is an enlarged cross-sectional view of the optical fiber taken along the line 6C-6C in FIG. 6B.

A first exposure processing is illustrated in FIGS. 6A to 6C. The used optical fibers 31 (for example, PJR-FB500 manufactured by TORAY INDUSTRIES, INC.) each have a diameter of 0.5 mm and has a double-layer structure including a core layer 31a formed on the inner side and a clad layer 31b formed on the outer side. Therefore, the presence of the clad layer 31b hinders efficient light irradiation from the respective optical fibers 31 at the time of bilirubin therapy. However, since a processing of breaking part of the clad layer 31b is performed, efficient irradiation is achieved. The processing of breaking means forming a row of round hole broken portions 31c on parts of the clad layer 31b of each of the optical fibers 31 placed in alignment, for example, by laser cutting. The light guided by the core layer 31a is dispersed by the round hole broken portions 31c and is irradiated or exposed upward (to the outside), and which acts effectively on the therapy. Since optical energy is strong near the side of the light guide portion 11 (the light source side) of the pad portion 12 and is weakened as it goes away therefrom, the intervals of the rows of the round hole broken portions 31c are set not to be dense on the light guide portion 11 side and to be denser as it goes away therefrom, so that the exposing light or irradiating light directed toward the patient may be homogenized.

Figure 7A:
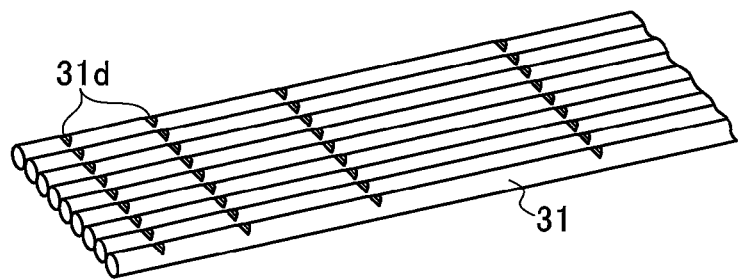
FIG. 7A is a perspective view illustrating a part of an example of a second exposed process of the optical fiber configuring the pad portion of the therapeutic portion of the same light-beam therapeutic apparatus.
Figure 7B:
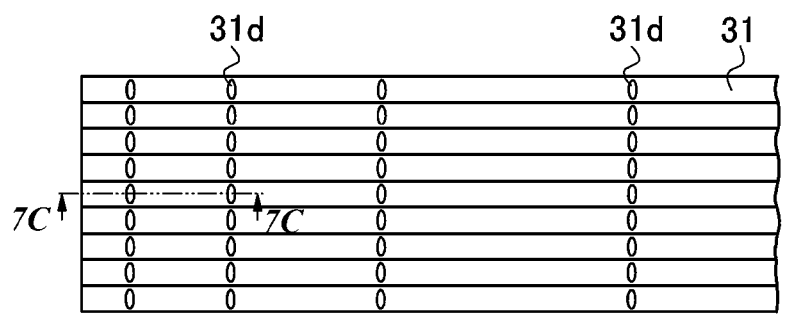
FIG. 7B is a plan view of the optical fiber illustrated in FIG. 7A.
Figure 7C:
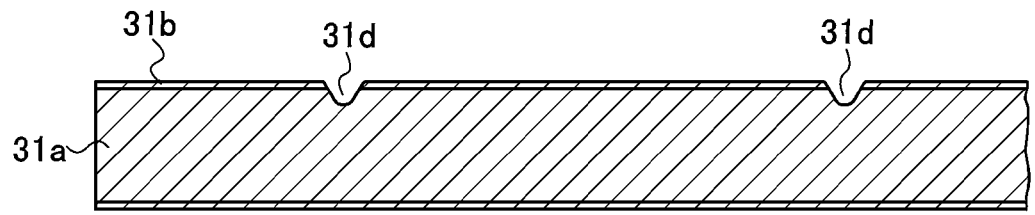
FIG. 7C is an enlarged cross-sectional view of the optical fiber taken along the line 7C-7C in FIG. 7B.

A second exposing processing is illustrated in FIGS. 7A to 7C. In the second exposing processing as well, oval broken portions 31d are formed in rows on parts of the clad layer 31b of each of the aligned optical fibers 31 by laser cutting in the same manner as the first exposing processing. The oval broken portions 31d increase the dispersion of the light guided by the core layer 31a, so that the therapeutic effect is increased. Also, in the same manner as the first exposing processing, the distance of the rows of the oval broken portions 31d are set not to be dense on the light guide portion 11 side, and is set to be denser as it goes away therefrom.

Figure 8A:
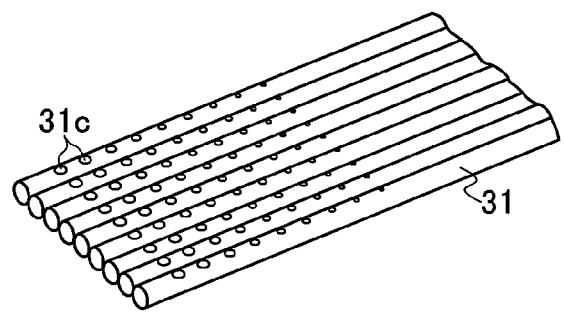
FIG. 8A is a perspective view illustrating a part of an example of a third exposed process of the optical fiber configuring the pad portion of the therapeutic portion of the same light-beam therapeutic apparatus.
Figure 8B:
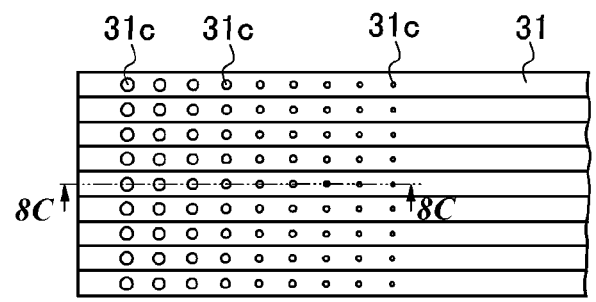
FIG. 8B is a plan view of the optical fiber illustrated in FIG. 8A.
Figure 8C:
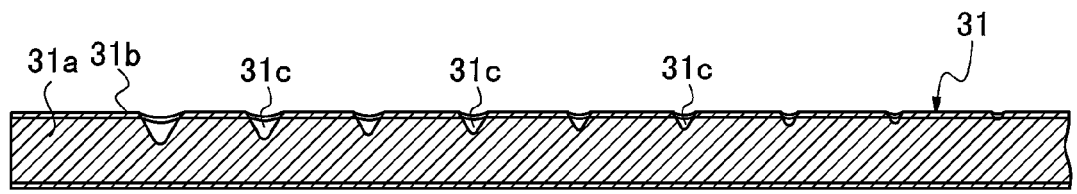
FIG. 8C is an enlarged cross-sectional view of the optical fiber taken along the line 8C-8C in FIG. 8B.

A third exposure processing is illustrated in FIGS. 8A to 8C. The third exposing processing forms the round hole broken portions 31c in the first exposing processing in a row, and is different from the first exposing processing in that the intervals of the rows are set to the regular intervals, and the sizes of the round hole broken portion 31c are set to be smaller on the light guide portion 11 side and larger and deeper little by little as it goes away therefrom. In this configuration, the homogenization of the light from a light-emitting surface is achieved.

Figure 9A:
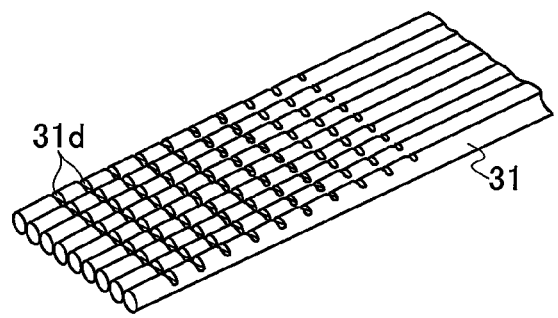
FIG. 9A is a perspective view illustrating a part of an example of a fourth exposed process of the optical fiber configuring the pad portion of the therapeutic portion of the same light-beam therapeutic apparatus.
Figure 9B:
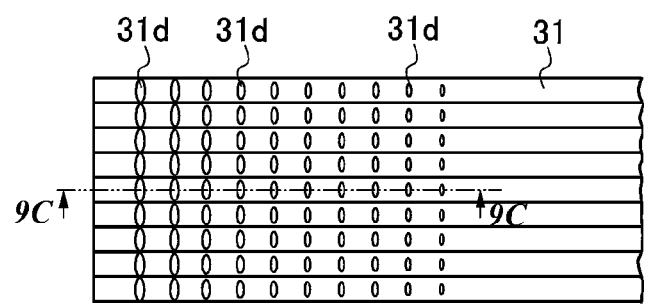
FIG. 9B is a plan view of the optical fiber illustrated in FIG. 9A.
Figure 9C:
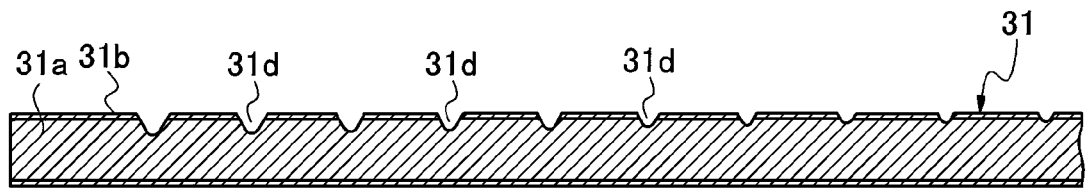
FIG. 9C is an enlarged cross-sectional view of the optical fiber taken along the line 9C-9C in FIG. 9B.

A fourth exposure processing is illustrated in FIGS. 9A to 9C. The fourth exposing processing forms the oval hole broken portions 31d in the second exposing processing in a row, and is different from the second exposing processing in that the intervals of the rows are set to the regular intervals as those of the third exposing processing, and the sizes of the oval broken portion 31d are set to be smaller on the light guide portion 11 side and larger and deeper little by little as it goes away therefrom. In this configuration, the homogenization of the light from the light-emitting surface is achieved.

The apparatus body portion 1 and the therapeutic portion 2 configured in this manner are configured to be connected to each other by inserting the plug 13 of the therapeutic portion 2 into the socket 4 of the apparatus body portion 1 as illustrated in FIG. 3, whereby an optical path formed in the light guide portion 11 including the light source 15, the light guide rod 17, and the plug 13 by the optical fibers 31 is established, so that preset light is irradiated from the pad portion 12. However, heat is generated by the light emission of the LEDs of the light source 15. The LEDs by themselves are maintained at a junction allowable temperature (125° C.) or below via the heat radiating member 19 by air supplied positively by the cooling fan 20. Therefore, the light guide rod 17 located on the irradiating side is irradiated with high-temperature light equal to or higher than the junction allowable temperature, so that the optical fibers 31 in the plug 13 opposing the light guide rod 17 may be melted due to high-temperature light and lose a light guiding function.

Therefore, in order to prevent such a situation, a translucent thermal insulation member 36 such as heat resistance glass is disposed between the light guide rod 17 and the plug 13 preferably at an end portion of the plug 13 in terms of convenience of maintenance. The thickness of the thermal insulation member 36 such as the heat resistance glass is selected from a range on the order of 1 to 3 mm so as not to impair the light guide function. In other words, the thermal insulation member 36 may be disposed in the optical path between the light source 15 and the pad portion 12.

Figure 10:
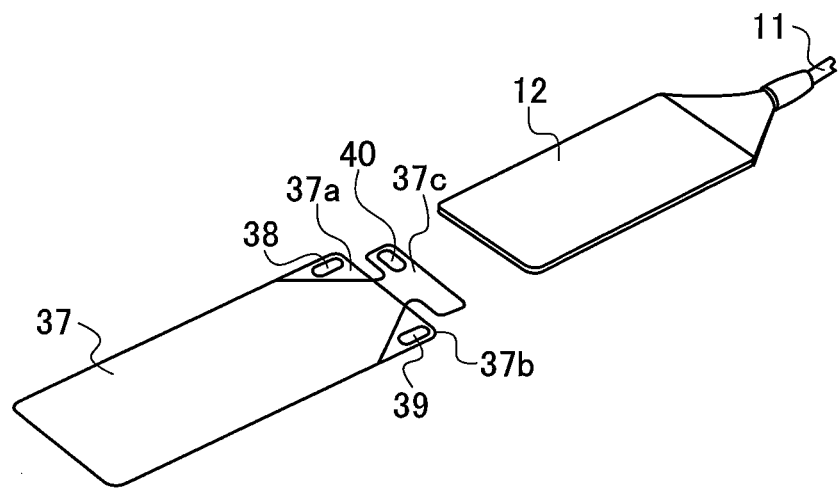
FIG. 10 is a perspective view schematically illustrating a pad cover to cover the pad portion of the therapeutic portion of the same light-beam therapeutic apparatus.
Figure 11:
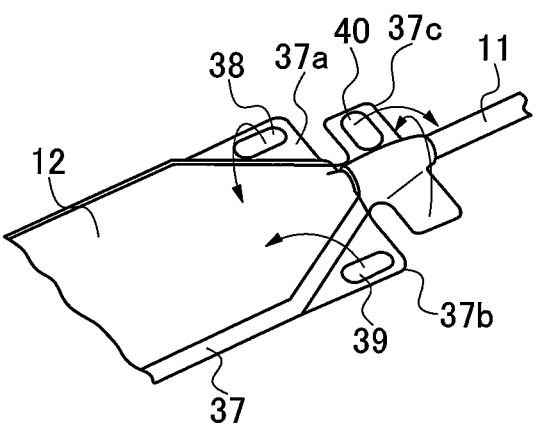
FIG. 11 is a partly enlarged perspective view illustrating a state in which the pad cover is covered on the pad portion of the therapeutic portion of the same light-beam therapeutic apparatus.

In actual use, as illustrated in FIG. 10 and FIG. 11, the pad portion 12 is covered with a pad cover 37 having the same shape. The pad cover 37 has a structure formed of water-absorbing, ecologically compatible, and highly flexible non-woven fabric, is formed into a bag shape as a whole, is formed with excessive protruding portions 37a, 37b, and 37c on the opening side, at least three fasteners 38, 39, and 40 such as an easy-to-stick device on the protruding portions so that the side provided with the fasteners corresponds to the back (lower surface) side. The pad cover 37 may be mounted by reversing the pad portion 12, reversing also the pad cover 37 and, in this state, inserting the pad portion 12 from the opening of the pad cover 37 and, as illustrated in FIG. 11, folding the respective protruding portions 37a, 37b, and 37c as indicated by arrows, and adhering the respective fasteners 38, 39, and 40 on the back side. In particular, the protruding portion 37c is mounted by winding it around the light guide portion 11 and adhering the fastener 40 on the wound protruding portion 37c. By mounting in this manner, the pad cover 37 is mounted on the pad portion 12 in a stable state. The pad cover 37 is disposable.

In a state in which the pad cover 37 is mounted on the pad portion 12 in this manner, the pad portion 12 is placed at a required place with the light-emitting surface faced upward, a neonatal infant is laid down on his or her back thereon, setting for the therapy is performed by operating the control display panel 3 of the apparatus body portion 1, and the therapy for the portion of the body where the pad portion 12 is in contact is efficiently achieved. In this case, even though the neonatal infant moves his or her body, since the protecting surface layer portion 35 filled with high-molecular gel is deformed so as to follow his or her movement, the delicate skin of the neonatal infant is prevented from being scratched or injured from bedsore.

The light-beam therapeutic apparatus of the invention is capable of not only performing a therapy for a neonatal infant having hyperbilirubinemia efficiently and adequately by irradiating his or her back portion for which the therapy cannot be performed usually because it is hidden entirely with homogeneous light beam, but also performing the therapy for the neonatal infant while holding the baby gently with the protecting surface layer portion even thought the neonatal infant moves, so that the apparatus may be applied widely to other therapies.

What is claimed is:

1. A light-beam therapeutic apparatus comprising:
    an apparatus body portion including at least a light source, a light guide rod configured to guide light from the light source, a connecting socket to which an end portion of the light guide rod faces, a cooling fan configured to cool the light source, an electronic component configured to perform control for a therapy, and a control display panel configured to display the contents of the therapy set by operating the electronic component; and
    a therapeutic portion including a light guide portion having a plurality of bundled optical fibers, and a pad portion at which the optical fibers are spread out adjacent to one another in a flat-panel shape,
    wherein an end portion of the light guide portion of the therapeutic portion includes a light-receiving plug to be inserted into the connecting socket of the apparatus body portion,
    the optical fibers positioned at the pad portion are subjected to exposing processing,
    the pad portion includes a protecting surface layer portion formed of a bag member filled with transparent and highly flexible high-molecular gel, the protecting surface layer portion protecting the optical fibers at the pad portion,
    each of the optical fibers has a two-layer structure including a core layer on an inner side thereof and a clad layer on an outer periphery thereof, the clad layer of each of the optical fibers having a group of broken portions which are broken by the exposing processing, and
    the group of broken portions are a plurality of round or oval holes formed in each of the clad layers and are configured to be arranged so that when the optical fibers are spread out adjacent to one another in the flat-panel shape each of the round or oval holes forming the group on an optical fiber are aligned in rows with each of corresponding round or oval holes forming the groups on the adjacent optical fiber so that exposing or irradiating light is homogeneously directed to a patient through the plurality of round or oval holes.

2. The light-beam therapeutic apparatus according to claim 1, wherein the light-receiving plug of the light guide portion is provided with a translucent thermal insulation member at an end portion thereof.

3. The light-beam therapeutic apparatus according to claim 1, further comprising a pad cover that covers the pad portion and is removable from the pad portion.

4. The light-beam therapeutic apparatus according to claim 1, wherein the plurality of round or oval holes are arranged at such intervals therebetween so as to be longer at a proximal end side of each of the optical fibers positioned at the pad portion when compared to a distal end, and shorter at a distal end side of each of the optical fibers positioned at the pad portion when compared to the proximal end side.

5. The light-beam therapeutic apparatus according to claim 1, wherein the plurality of round or oval holes are configured to have such sizes thereof so as to be smaller at a proximal end side of each of the optical fibers positioned at the pad portion when compared to a distal end, and greater at a distal end side of each of the aligned optical fibers positioned at the pad portion when compared to the proximal end side.

6. The light-beam therapeutic apparatus according to claim 1, wherein the plurality of round or oval holes are configured to have such depths thereof so as to be shallower at a proximal end side of each of the optical fibers positioned at the pad portion when compared to a distal end, and deeper at a distal end side of each of the aligned optical fibers positioned at the pad portion when compared to the proximal end side.

* * * * *